(12) United States Patent
Yadav et al.

(10) Patent No.: US 6,813,931 B2
(45) Date of Patent: Nov. 9, 2004

(54) NANOCOMPOSITE DEVICES AND RELATED NANOTECHNOLOGY

(75) Inventors: Tapesh Yadav, Tucson, AZ (US); Clayton Kostlecky, Longmont, CO (US); Anthony Vigliotti, Tucson, AZ (US)

(73) Assignee: NanoProducts Corporation, Longmont, CO (US)

(*) Notice: Subject to any disclaimer, the term of this patent is extended or adjusted under 35 U.S.C. 154(b) by 109 days.

(21) Appl. No.: 10/001,423

(22) Filed: Dec. 3, 2001

(65) Prior Publication Data

US 2002/0184939 A1 Dec. 12, 2002

Related U.S. Application Data (62) Division of application No. 09/753,806, filed on Jan. 3, 2001, now Pat. No. 6,513,362, which is a division of application No. 09/074,534, filed on May 7, 1998, now Pat. No. 6,202,471.

(60) Provisional application No. 60/061,718, filed on Oct. 10, 1997, and provisional application No. 60/068,121, filed on Dec. 19, 1997.

(51) Int. Cl.[7] ............................................. G01N 17/00
(52) U.S. Cl. .................................................... 73/31.05
(58) Field of Search .......................... 73/23.31, 23.2, 73/25.01, 31.05, 29.05; 324/663, 664; 361/280; 427/58, 79, 126.1, 126.6; 338/34, 35; 422/98; 204/424, 425

(56) References Cited

U.S. PATENT DOCUMENTS

| | | | | |
|---|---|---|---|---|
| 4,581,204 A | * | 4/1986 | Voit | 422/90 |
| 4,931,851 A | * | 6/1990 | Sibbald et al. | 257/414 |
| 5,065,140 A | * | 11/1991 | Neuburger | 340/634 |
| 5,170,226 A | * | 12/1992 | Fukuzawa et al. | 257/14 |
| 5,486,277 A | * | 1/1996 | Barbee et al. | 204/192.15 |
| 5,548,474 A | * | 8/1996 | Chen et al. | 361/313 |
| 5,670,115 A | * | 9/1997 | Cheng et al. | 422/90 |
| 5,685,969 A | * | 11/1997 | Hoenig et al. | 205/123 |
| 5,905,000 A | * | 5/1999 | Yadav et al. | 429/33 |
| 5,952,040 A | * | 9/1999 | Yadav et al. | 427/126.3 |
| 6,228,904 B1 | * | 5/2001 | Yadav et al. | 523/210 |

FOREIGN PATENT DOCUMENTS

JP 0826979 * 11/1996

* cited by examiner

*Primary Examiner*—Robert Raevis
(74) *Attorney, Agent, or Firm*—Stuart T. Langley; Hogan & Hartson LLP (57) ABSTRACT

Nano-engineered devices exhibiting quantum effect and methods for forming such devices from nanomaterials are disclosed. Multilaminated sensing, piezoelectric, photonic, biomedical and thermal devices are taught. The composition included are chalcogenides, oxides, nitrides, borides, carbides, phosphides, halides, silicate, hydrides, oxynitrides, oxycarbides and other complex nanomaterial composition.

22 Claims, 4 Drawing Sheets

NANOCOMPOSITE DEVICES AND RELATED NANOTECHNOLOGY

This application is a divisional of U.S. patent application Ser. No. 09/753,806, now U.S. Pat. No. 6,513,362 titled "LOW-COST MULTI-LAMINATE SENSORS," filed Jan. 3, 2001, which is a divisional of U.S. patent application Ser. No. 09/074,534, titled "LOW-COST MULTI-LAMINATE SENSORS," filed May 7, 1998, now issued as U.S. Pat. No. 6,202,471, which claims the benefit of priority to U.S. Provisional Patent Application No. 60/061,718, filed Oct. 10, 1997, and No. 60/068,121, filed Dec. 19, 1997.

BACKGROUND OF THE INVENTION

The ability to detect the presence and composition of chemical species has been an important goal for several reasons. For example, the detrimental environmental effects of toxic species such as formaldehyde, carbon monoxide, ozone, hydrocarbons, chlorocarbons, nitrogen oxides, aromatics and heavy metals has led to the need to develop efficient, sensitive, and affordable ways of detecting the composition and presence of such toxic substances. Additionally, the efficiency of chemical processes, in terms of energy and raw material used per unit product or service delivered, relies on the ability of the overall system to reliably sense deviations from the optimal processing conditions. Since process efficiencies directly determine the overall costs of the process and indirectly determine the wastes generated by the process, it is critically important that a method be available that can provide the necessary feedback about the process (sensors) and initiate actions to evolve the system parameters to the optimal levels (actuators).

The temperature, pressure and flow monitoring and control of chemical, environmental, biochemical, biomedical, geological, metallurgical, and physical processes have been extensively researched and the state-of-the-art technologies quite effectively enable real-time evolution of the monitored process. However, compositional monitoring and control of these processes leaves much to be desired. Crude methods for process monitoring and control are based upon batch analysis, i.e., a statistical set of samples are obtained ("grab sample" approach) and then analyzed for composition. These data are then interpreted and actions are initiated to control the process to desired levels. The response time for such a strategy often is in days, if not weeks. This strategy has serious deficiencies since it inherently accepts inefficient operation between the time the samples were obtained and the actions are initiated to correct deviations from the optimal. Yet another deficiency in such a strategy is that it overlooks the possibility that the process conditions may have changed during the response and analysis lag time.

Alternatively, sophisticated monitors (such as gas chromatographs with suitable sampling and transport systems) have been integrated into the processes. These systems are expensive, bulky, not suited for extreme temperatures and pressures, and have response times that are more than a few minutes. Real-time composition monitoring and control of the chemical and combustion processes require sensors that overcome these limitations. Specifically, sensor technology for gas sensing applications should ideally be selective, sensitive to trace species, fast (short response time), small, accurate, reproducible, stable in extreme environments, durable (long life), and affordable.

Prior art methods for producing gas sensors include those of U.S. Pat. No. 4,631,952 which teaches a method of preparing a sensor by the formation of a dispersion of conducting particles with a material capable of swelling in the presence of the liquid, gas or vapor to be sensed. Furthermore, U.S. Pat. No. 4,984,446 teaches the preparation of a gas detecting device by a layer by layer build up process, and U.S. Pat. No. 4,988,539 teaches an evaporation-deposition method and process for manufacturing a gas detection sensor. Finally, U.S. Pat. No. 5,387,462 teaches a method of making a sensor for gas, vapor, and liquid from a composite article with an electrically conductive surface having an array of whisker-like microstructures with an aspect ratio of 3:1 to 100:1.

Although these prior methods provide improved methods for producing sensors, there is still a need to develop sensors that are selective, sensitive to trace species, fast, small, accurate, reproducible, stable in extreme environments, durable, and finally affordable.

SUMMARY OF THE INVENTION

In one aspect, the present invention involves a sensor device comprising a laminated structure including multiple sensing and/or electrode layers, each of which may be of the same or different compositions. The structure may have 3–500 layers, or in other embodiments 10–100 layers, or in yet other embodiments 20–50 layers. The slices may be calcined and sintered before they are cut. The sensor may be partially or completely coated, for example to protect the electrodes from environmental damage. The sensing layers may be prepared using powders or composites, e.g., nanostructured powders and nanocomposites. The interaction between the sensor and the analyte may be physical, chemical, electronic, electrical, magnetic, structural, thermal, optical, surface, or some combination. The sensor may include layers other than the sensing and electrode layers, for example, heating or insulating layers.

DEFINITIONS

"Sensitivity," as that term is used herein, is a dimensionless measure equal to the ratio of the change in a measured property to the original value of that property. For example, the sensitivity of a chemical sensor whose resistance is a function of chemical environment is defined as $((R_a-R_s)/R_a)$ where $R_a$ represents the resistance of the sensor in the absence of the sensed chemical species, and $R_s$ represents the resistance of the sensor in the presence of the sensed chemical species.

DESCRIPTION OF THE DRAWINGS

The invention is described with reference to the several figures of the drawing, in which.

DESCRIPTION OF CERTAIN PREFERRED EMBODIMENTS

In one aspect, the present invention provides sensing devices and, more specifically, chemical composition sensors and a fluid composition sensors. Additionally, a method for the use of a chemical composition sensor to detect the composition of a species of particular interest is disclosed in the presently claimed invention. In another aspect, the present invention provides novel fluid and chemical composition sensors for detecting the presence and composition of liquids, vapors, and gases.

According to the presently claimed invention, the method for the synthesis of a chemical composition sensor or a fluid composition sensor involves selecting a particular species of interest and then selecting a particular material composition that is capable of interacting with the species of interest. If the selected material composition is capable of interacting simultaneously with multiple species of interest, compositions that interact equally with two or more species are preferred for the practice of the invention. In a preferred embodiment, the material compositions interact with one species. In another preferred embodiment, the material composition may interact with up to (n−1) species where n is the number of species. In yet another preferred embodiment, the material composition may interact with all n species on an unequal basis. In all cases, this invention requires that the selected material compositions be physically robust in presence of all species in its environment for a duration equal to or greater than the desired life for the sensor. It is also desirable that more than n such material compositions are identified and used, because, in the event that one element fails, the redundant elements provide the necessary signal for reliable operation of the sensor.

The interaction of the species with the material composition in this invention necessarily requires that the material's properties detectably change when the species and material composition are exposed to each other materially, mechanically, thermally, optically, or electromagnetically, or a combination of these. Any property change which can be reliably detected with a satisfactory signal-to-noise ratio may be used, including physical changes, chemical changes, electrical and electronic changes, magnetic changes, structural changes, optical changes, thermal changes, surface changes, or any combination of these. In preferred embodiments, physical interactions include but are not limited to adsorption, absorption, expansion, shrinkage, and phase transformation. In other preferred embodiments, chemical interactions include but are not limited to reaction with the material, isomerization, dissociation, and polymerization. In yet other preferred embodiments, electrical and electronic interactions include but are not limited to changes in dielectric constants, charge transfer, and hole transfer.

Once a suitable material composition has been selected for use in the chemical composition sensor, in one embodiment, namely the formation of a chemical composition sensor, a laminated stack structure 10 (FIG. 1), preferably multi-layer, is formed using the identified sensing material. The laminated stack contains at least one sensing layer 12, and at least one electrode layer 14. The sensor shown in FIG. 1 also comprises electrical terminals 16, in electrical communication with the electrode layers 14.

Figure 1:
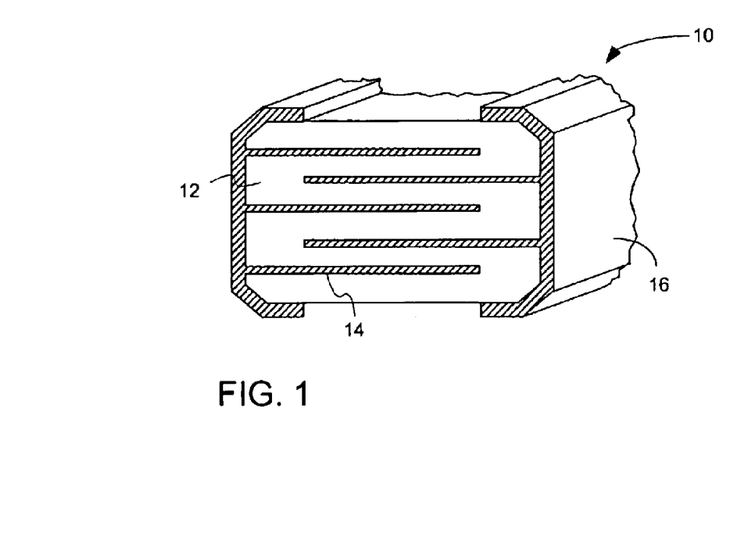
FIG. 1 depicts a diagram of a laminated multi-layer sensor according to the invention.

The sensing layer 12 can be formed by any method, including but not limited to spin coating, dip coating, powder pressing, tape casting, screen printing, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, 25 thermophoretic deposition, stamping, centrifugal casting, gel casting, extrusion, electrochemical deposition, screen-stencil printing, brush painting, or a combination of one or more of the above-mentioned methods. The sensing layer thickness can be in the range of 1 nm to 10 cm, a preferred thickness being less than 100 microns, a more preferred thickness being less than 10 microns, and a most preferred thickness being less than 1 micron. In a preferred embodiment, the sensing layer can also be doped with catalysts to further enhance the selectivity of interaction or the kinetics of interaction, or doped with promoters to enhance the ability to detect the changes in the properties of the material composition. These secondary treatments of the sensing layer may enhance the performance of the sensing layer.

Possible compositions of the sensing layer include but are not limited to organic, inorganic, metallic, alloy, ceramic, conducting polymer, non-conducting polymer, ion conducting, non-metallic, ceramic-ceramic composite, ceramic-polymer 10 composite, ceramic-metal composite, metal-polymer composite, polymer-polymer composite, metal-metal composite, processed materials including paper and fibers, and natural materials such as mica, bio-organisms, biologically active materials, biologically derived materials, biocomposites, or a combination of one or more of these. Illustrative compositions include but are not limited to doped or un-doped, stoichiometric or non-stoichiometric titanium oxide, barium titanate, strontium titanate, zinc oxide, indium oxide, zirconium oxide, tin oxide, antimony oxide, tungsten oxide, molybdenum oxide, tantalum oxide, cerium oxide, rare earth oxides, silicon carbide, bismuth telluride, gallium nitride, silicon, germanium, iron oxide, titanium boride, iron boride, zirconates, aluminates, tungstates, carbides, borates, hydrides, oxides, oxynitrides, oxycarbides, halides, silicates, phosphides, nitrides, chalcogenides, complex oxides such as dielectrics and ferrites, enzymes, nucleotides, antibodies, cells, and polymers.

Additionally, the sensing layer can be porous or dense, flat or tapered, uniform or non-uniform, planar or wavy, straight or curved, non-patterned or patterned, micron or sub-micron, grain sized confined or not, or a combination of one or more of these.

In preferred embodiments, the electrode layer 14, as shown in FIG. 1, may comprise any composition that conducts the signal more easily than the sensing layer, most preferably with a lower impedance than the sensing layer. If the signal is electrical signal, the electrode layer is any composition that conducts electricity more easily than the sensing layer, preferably with a lower impedance than the sensing layer. It is most preferred that the electrode impedance be very low, preferably below 10% of the sensing material layer's impedance. In case properties other than electrical are utilized for sensing, the impedance to the signal should be less in the electrode layer than the sensing layer. If the impedance of the electrode is high, then it is preferable that the electrode impedance be predictable and that the metrology compensate for the electrode impedance to achieve satisfactory signal to noise ratio. The composition of the electrode layer can include, but is not limited to, organic materials, inorganic materials, metallic, alloy, ceramic, polymer, non-metallic, ceramic-ceramic composite, ceramic-polymer composite, ceramic-metal composite, metal-polymer composite, polymer-polymer composite, metal-metal composite, or a combination of one or more of these. Geometries may be porous or dense, flat or tapered, uniform or non-uniform, planar or wavy, straight or curved, non-patterned or patterned, micron or sub-micron, grain size confined or not, or a combination of one or more of these. Methods of forming the electrode layer include but are not limited to spin coating, dip coating, powder pressing, tape casting, screen printing, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, thermophoretic deposition, stamping, centrifugal casting, gel casting, extrusion, electrochemical deposition, screen and stencil printing, brush painting, or a combination of one or more of such methods.

As shown in FIG. 1, the sensor is comprised of laminated layers of sensing layers 12 and electrodes 14. The sensor may just have one layer or multiple layers, the preferred embodiment being multiple layers. The individual sensing layers or electrodes can be the same or different formulation. Additionally, it is possible to replace or combine one of the sensing layers with a layer capable of a secondary but desired function. For example, the sensing layer can be replaced with resistive layers by design to provide heat to the sensor. In some situations it may be desirable to have one or more sensing layers replaced with EMI (electromagnetic interference) filter layers to minimize noise by inductively or capacitively coupling with the sensing layer. In another situation, one of the layers can be air or an insulating layer in order to provide thermal isolation to the active layer. In yet another situation, electrochemical couple layers may be provided to internally generated electricity and energy needed to satisfactorily operate the sensor. In other conditions, the electrode layers can function as anodes and cathodes. In some situations, the sensor may be a minor part of the multi-laminate device and the sensor containing device can have primary function of reliably providing an electrical, thermal, magnetic, electromagnetic, optical, or structural function in an application. The sensing layer can also comprise multi-laminates of different material formulations.

The multi-layer stack 10, as shown in FIG. 1, has a rectangular shape. However, the stack shape can also be circular, elliptical or any other shape. Additionally, the edges may be rounded or sharp. The electrodes in the multi-layer stack can be connected to yield a single sensor element structure or connected selectively to yield a sensor array. Furthermore, in case of arrays, common electrodes for two or more sensors may be used to reduce the external lead costs and crowding. The termination can similarly be internal or external to satisfy the particular needs of an application.

Figures 2A, 2B:
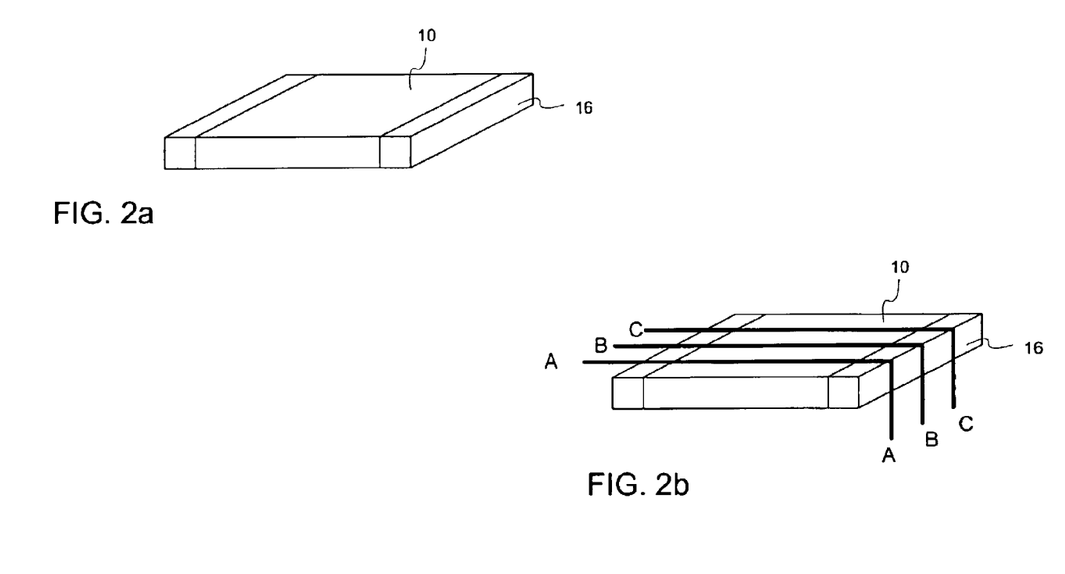
FIG. 2a, FIG. 2b and FIG. 2c depicts the process of terminating and cutting a laminated stack to produce the sensor shown in FIG. 1.
Figure 2C:
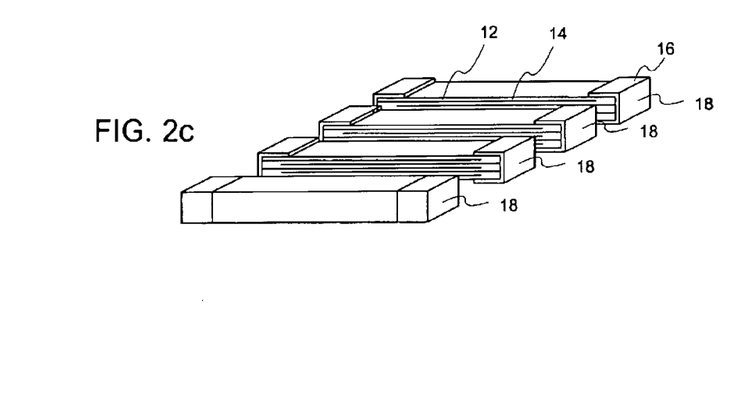
Figure 3:
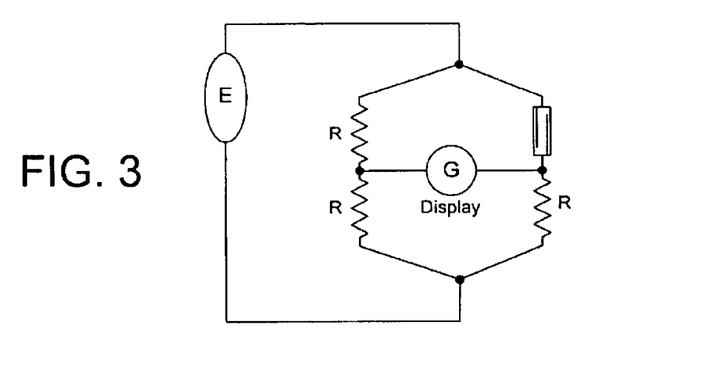
FIG. 3 is a circuit diagram illustrating the use of the sensor depicted in FIG. 1.

After preparation of a multi-layer stack, the stack may then be cut cross sectionally into thin slices to expose the alternating layers of the sensing layer and the electrode. FIG. 2a shows a terminated stack 10, which is saw cut along lines A—A, B—B, and C—C as shown in FIG. 2b. FIG. 2c shows the exposed alternating layers at the surfaces of the slices 18. Each slice is a device which can be used in a circuit shown as FIG. 3 to detect the composition of an analyte in a gas, vapor, liquid or a combination of these. The circuit shown in FIG. 3 is illustrative; it may be replaced with any suitable circuit that can detect the signal to noise ratio acceptable in a given application.

The multi-layer stack can be a single element or an array of sensing elements. In the case of a single element body, single element sensors result after the slicing operation. In the case of an array element body, an array of sensor elements results after the slicing operation. After the slicing operation, the exposed cut surfaces provide the sensing surfaces, while the unexposed surfaces isolate the device. The electrodes of the device provide means to connect the sensor to an external circuit and obtain the signal.

In a preferred embodiment, it is desirable that the sensing layers and the electrode layers be isolated from external environmental damage such as that from thermal, mechanical, chemical, electrical, magnetic, or radiation effects, or a combination of one or more of these. This desired protection can be achieved by providing a conformal covering over the layers on the unexposed surfaces, such as a polymer conformal protective layer. In another preferred embodiment, the exposed surface may also be isolated from external thermal, mechanical, chemical, electrical, magnetic, or radiation damage by covering with a layer of ceramic or porous rigid material mesh. In yet another preferred embodiment, the exposed surface may also be covered with a layer that enhances the selectivity of the analyte reaching the sensing surface. Such a layer can include, but is not limited to, polymers, metals, zeolites, or porous media, each of which has a higher permeability for the analyte of interest and a lower permeability for other species that are not of interest. In some preferred embodiments the exposed surface is covered with polyethylene, polypropylene, Teflon, polycarbonates, or polyaromatics. However, it is generally preferable that any covering on the exposed surface does not impede the interaction of the analyte or analytes to be sensed with the active sensing layer by an amount greater than the species that are not of interest. Exceptions to this general rule maybe made in certain cases, for example, when it is critical to protect the element from destructive effects of the environment.

In a preferred embodiment of the present invention, the sliced sensor elements are also calibrated. The calibration is preferably performed with a gas, vapor, or liquid mixture whose composition of one of the desired species is varied. During the calibration, the impedance value versus the concentration of the varying species is obtained. Such calibration data is preferably obtained for all species of interest. In the event that only complex data is available, pattern-matching software (e.g., neural networks) can be utilized to correlate the response of the device to each specific analyte.

In another particularly preferred embodiment, a method for manufacturing a fluid composition sensor is provided. This method involves selecting a chemical species of interest, selecting a material composition that selectively interacts with the species of interest, preparing a quantum confined or nanometer cluster form of the selected sensing material, preparing thin monolithic or composite film arrays of quantum confined or nanocluster forms of sensing materials, and finally connecting leads to form the sensor array.

Figure 4A:
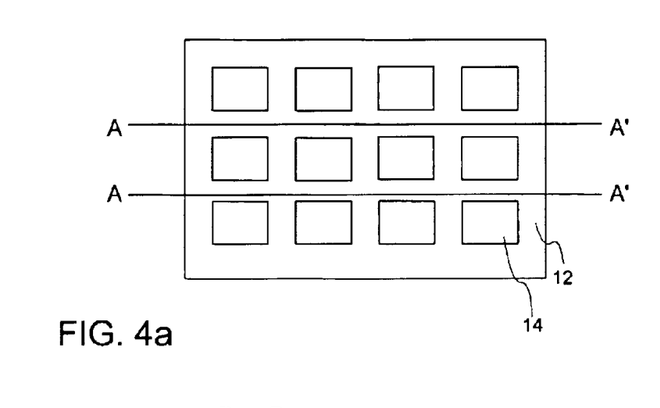
FIG. 4a and FIG. 4b shows an illustrative electrode pattern for the sensors of the invention.
Figure 4B:
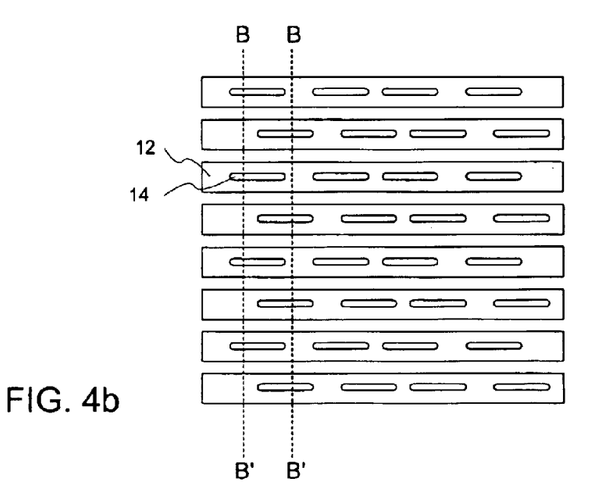

The selection of the chemical species of interest and the selection of the material composition has previously been discussed with regard to the manufacture of the chemical composition sensor. Subsequently, quantum confined and nanometer cluster forms of the identified material compositions are prepared. In preferred embodiments, this can be accomplished by chemical precipitation techniques, vapor condensation, thermal quench, pyrolysis, mechanical alloying, explosive or chemical disintegration, laser beam evaporation, template synthesis, or a combination of these methods. Once the quantum confined and nanometer cluster form of the material compositions are available that interact with the species of interest, laminated thin films of the sensing materials are prepared on electroded substrates. The electrodes are provided to enable the measurement of impedance changes in the film with composition changes. In particularly preferred embodiments, the electrodes are prepared by screen printing, tape casting, spraying, sputtering, chemical vapor deposition, physical vapor deposition, epitaxy, electrochemical deposition, mold stamping, and cutting through a multilayer to expose the electrodes. It is particularly preferred that the electrodes be uniform, without sharp edges, and reproducible between the sensors. FIG. 4 shows two views of an illustrative electrode pattern. The electrodes 14 in this pattern can be exposed for termination by cutting at lines A–A' and B–B'. For selectivity, in a preferred embodiment, one may integrate a resistive element in the substrate to heat the sensor to a desirable temperature to facilitate the interaction of the species of interest to the material composition as desired. However, if the heating element is integrated, care must be taken to avoid shorting of the electrode or transmission of noise from resistive element to impedance signal from the electrode. This can be accomplished with the use of capacitive, resistive, or inductive film, or a combination thereof.

Once the electroded substrate is available, the quantum confined and nanometer cluster form of the material is formed into thin or thick films preferably using, but not limited to, one of the following manufacturing methods or a combination thereof including masked screen printing, masked tape casting, masked spraying, masked sputtering of nanostructured targets, masked vapor deposition, masked epitaxy, masked electrochemical or electrophoretic deposition of cluster, and masked mold stamping. In a most preferred embodiment, a single manufacturing method is used to prepare all sensing elements in a sensor. Since the presently claimed invention requires that elements of different material compositions be deposited to detect different species of interest, it is inherent to change the mask and repeat the element-forming step.

After the step of forming the films, the film is preferably dried and sintered at low temperatures to ensure mechanical robustness. The use of low temperatures is preferred because high temperatures can cause grain growth and consequent loss of surface area and confinement-related properties. It is particularly preferred that the sintering temperatures be less than $0.75T_m$, where $T_m$ is the melting point of the film's material. If necessary, higher temperatures can be used, however it is then preferred that the sintering time be minimized.

Once the film on the electrode has been deposited, the leads are connected to the electrodes. To minimize the costs, it is preferred that a common electrode be used. The common electrode is one that connects all the sensor elements. The second free electrode of each element is next used to determine the impedance of each element as a function of the sensor element's environment.

Finally, after the sensor elements have been produced, they are calibrated. The calibration is preferably performed with a gas mixture whose composition varies only in one of the desired species. The impedance value versus the concentration of the varying species is obtained. Such calibration data is then obtained for all species of interest. In the event that only complex data is available, pattern-matching software such as neural networks can be employed.

The novel chemical composition sensors and fluid composition sensors as described can be utilized to determine the composition and presence of vapors, gases, and liquid analytes. The sensor element or array can be connected in a circuit to prepare a monitor capable of detecting changes in the property of the sensing layer. The sensor may be used as a disposable sensor or as a non-disposable sensor, as a regenerable or non-regenerable sensor, or as a continuous or cumulative sensor. In a particularly preferred method, the sensor element or sensor element array is first exposed to the environment whose composition needs to be measured. The sensing mechanism can be based, for example, on resistance, capacitance, inductance, impedance, phase angle, loss factor, dissipation, breakdown voltage, electrical temperature coefficient of an electrical property, Nernst current, impedance associated with ion conducting, open circuit potential, electrochemical property, electronic property, magnetic property, thermal property, mechanical property, or optical property. In a particularly preferred embodiment, the impedance value is obtained and interpreted in light of the calibration data. The interpreted impedance then yields the desired composition information. One of ordinary skill in the art will appreciate that particular sensor designs and sensing layer properties are specifically designed to detect particular compositions. Therefore, the choice of particular sensor designs and sensing layer properties may limit the potential use of the sensor elements or arrays.

The examples presented below are intended to more particularly describe the present invention, but are not intended to limit the scope of the presently claimed invention.

EXAMPLES

Example 1

Multi-layer ZnO Sensor

Figure 5A:
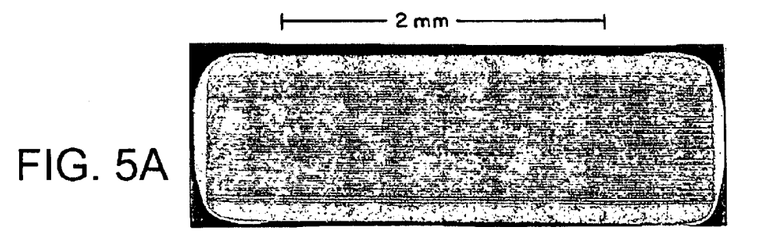
FIG. 5a and FIG. 5b are is-a backscatter images of the sensor of Example 1.
Figure 5B:
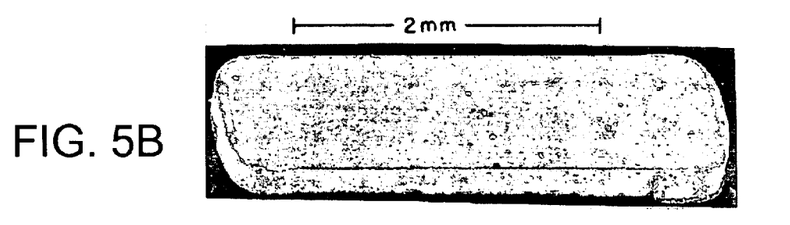
Figure 6:
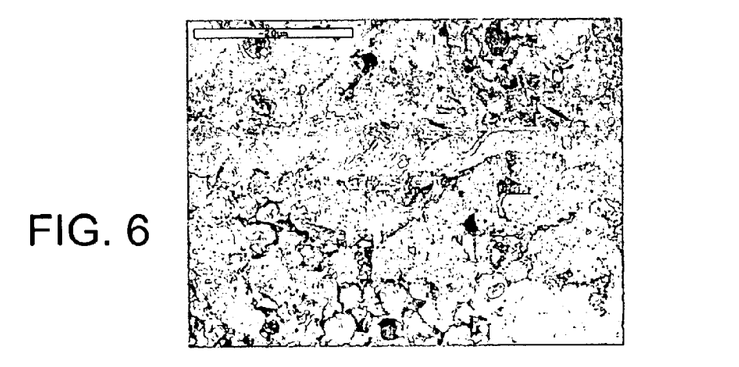
FIG. 6 is a SEM micrograph of the sensor of Example 1.

Multi-layer Pt/ZnO/Pt structures of initial size 0.125"×0.100"×0.058" (L×W×H) having 12 layers of ZnO were lapped and polished to expose the active multi-layered sensor surface as follows: After mounting the samples on the polishing surface with a crystal bond wax, they were then polished to 600 grit on both sides. The final components shown in the backscatter images (FIG. 5) had dimensions of 0.125×0.100×0.029 (L×W×H), and gave a high level of contrast between the 12 active layers and the interlocking electrodes. FIG. 6 offers a close-up of the interlayer electrode and shows some of the porosity of the samples. The grain size in the multi-layer structure was on the order of several microns. The devices were then mounted on an alumina substrate and leaded with a silver-based epoxy for leads.

Figure 7:
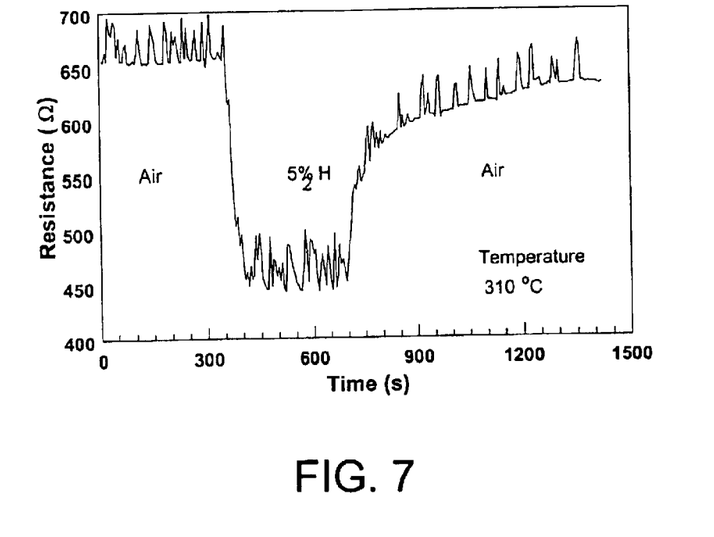
FIG. 7 presents the response data of the sensor of Example 1 to 5% hydrogen gas.

The sensor was tested in air (200 ml/min) and the resistance of the sensor element was measured as a function of changes in air composition. The testing of the devices revealed that the devices were sensitive to moisture, to temperature, and to reducing gases. FIG. 7 shows the response of the device to 5% hydrogen gas. There is a decrease in the resistivity of the device on switching to hydrogen and an increase on switching back to air. Some EMI noise is apparent in the data due to the way the meter makes the measurement. Other measurements confirmed that the EMI noise can be eliminated.

Figure 8:
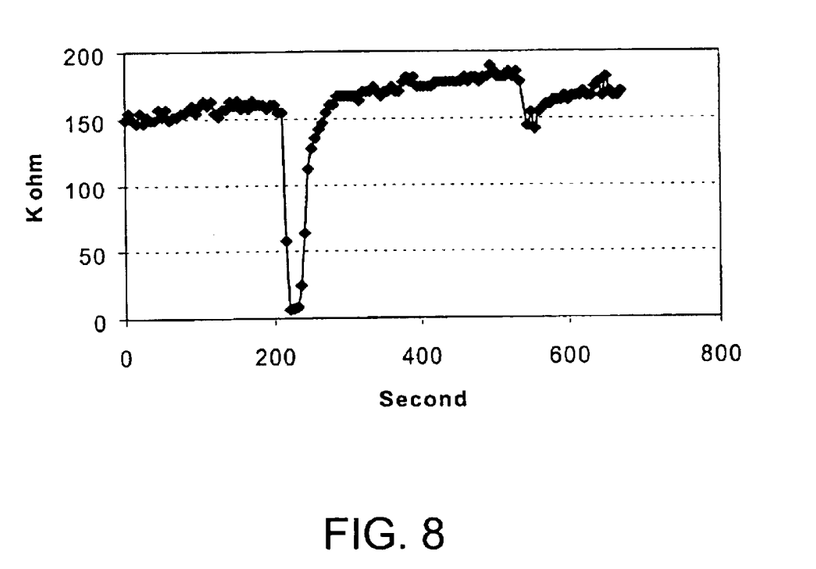
FIG. 8 presents the response data of the sensor of Example 1 to water vapor.

Further experiments confirmed that the multi-layer structure has high response to moisture. FIG. 8 presents the response data. The sensitivity of the sensor to water vapor in air was found to be 15 and the response time was less than 5 seconds.

The sensor was also responsive carbon monoxide. The sensitivity of the sensor to carbon monoxide was 0.15 and response time was over a minute. The sensor had no response to methane, which suggests that the sensor is sensitive to certain reducing gases, but not all reducing gases. The sensor showed no response to an oxidizing environment.

Example 2

Sensor Using Inductance and Capacitance Changes

Non-stoichiometric barium strontium titanate ($BaSrTiO_3$) multi-layer structures of 1812 EIA standard capacitor size and NPO formulation were ground on a 40 micron diamond pad exposing the multi-layer surface and leaving an interdigital electrode with the sensing material between the fingers of the electrodes. The sensor surfaces were then polished with 9 micron diamond paste. Five different sensors produced in this manner were tested to establish reproducibility of the performance. First each sensor was exposed to 200 ml/min of nitrogen for one minute to establish a base line. Next, the sensor environment was changed to 200 ml/min of analyte containing nitrogen. Finally, the sensor environment was changed back to pure nitrogen. The capacitance of each sensor was measured as a function of gas composition. Sensors were sensitive to hydrogen at temperatures higher than 550° C., demonstrating the device's usefulness for high temperature applications. The response time was about 1 minute and the sensitivity was about 0.45. At temperatures higher than 600° C., the sensor was found to exhibit changes in inductance as well (inductive selectivity to hydrogen was about 20.0 at 619° C. and response time was less than 5 seconds). This demonstrates that the sensor's capacitance and inductance are also alternative usable signals for sensor metrology.

Example 3

Single Laminate Chemical Composition Sensor

Nano ITO powders ($In_2O_3$: $SnO_2$=1:9 wt/wt %) were prepared using chemical precipitation. Indium (III) chloride (Aldrich, as received) 100 g was dissolved in 40 ml water with the addition of 70% $HNO_3$. Then 12.896 g of 61.55% $SnCl_4$ solution was added to the $InCl_3$ solution. Constant agitation was maintained using a magnet stir bar. The indium and tin chloride solution was titrated using 14% $NH_3$ solution until the pH of the solution turned to around 10. During the titration, the clear solution turned to milk white slurry. The slurry was filtered under vacuum, and washed first with water, then with denatured ethyl alcohol, and finally with cyclohexane. The resulting cake was dried at 100° C. for 3 hours, yielding fine white powders. The powders so produced were ball-milled for 5 hours followed by calcination at 450° C. for 30 minutes, leading to yellow ITO powders. Then ITO powders were characterized with X-ray diffractometer which indicated that the size of the powders were about 13.5 nanometers.

To prepare the sensor; first a discontinuous, interdigitated gold electrode was screen printed on alumina substrate. A single sensing layer laminate was then deposited as follows: 100 ml 0.1 M pyrrole and 0.5 M KCl solution was first prepared, and dispensed into a vial with 83.3 mg of a biospecies-glucose oxidase (Sigma, G6766). Then 300 1 pyrrole-biospecies solution was pipetted and galvanized under 1.0 A for 2 minutes with Ag/AgCl as reference electrode, platinum as counter electrode, and interdigitated gold electrodes prepared above as working electrodes. A thin layer of polypyrrole film was formed onto the interdigitated gold electrodes under galvanization, and biospecies were grafted on the polypyrrole nanocomposite film.

The prototype nanocomposite sensors were tested with 2000 ppm trichloroethylene (TCE) in zero-grade synthetic air. The gas flow rate was controlled with Mass Flow Controller at 200 ml/minute, and the sensor testing temperature was kept at room temperature (22° C.~23° C.). The resistance spectra were recorded with Quicklog interface and software from Omega Engineering, Inc. The results show that the sensors had good sensitivity for dichloromethane and trichloroethylene. The sensitivity (($R_a-R_s$)/$R_a$) was 0.15 for dichloromethane and 0.10 for trichloroethylene. The response time was less than 10 seconds.

Example 4

Single Laminate Nanocomposite Sensors for Explosive Vapors 0.5 grams of Tin Oxide ($SnO_2$) nanopowders with a specific surface area of 56.1 $m^2$/g were mixed in a solution of 0.005 g/ml of poly(ethylene glycol) binder dissolved in isopropanol and the mixture was sonicated for 20 minutes, producing a thick slurry The prepared slurry was deposited onto an alumina substrate with pre-printed electrodes, using spin coating at a rotation speed of about 1000 rpm. Each spin coating process yielded a single laminate thin film nanocomposite sensor. To examine the effect of catalyst dopant on the nanocomposite sensor performance, a 2% solution of Pt/Pd catalyst in water was prepared and about 1–2 microliter was deposited, using syringe, onto the surface of some sensor prototype films. The catalyst immediately spread out over the entire surface of the film and dried in a few minutes. The sensor elements were 5 tested with explosive stimulant vapors (Sigma/Aldrich, as received) as the analyte and 200 ml/min air as the carrier gas.

Table 1 shows a summary of the sensitivities and response times for sets of deposited $SnO_2$ sensors to analytes as room temperature or higher.

TABLE I

Sensor response to (3 ppm) analyte in 200 ml/minute

| Sensing Material | Analyte | Temp. (CO) | Sensitivity (Rair Rg)/Rg | Response Time (seconds) |
|---|---|---|---|---|
| Nanocomposite | Explosive | 21 | 26% | 65 |
| Nanocomposite + Catalyst | Explosive | 21 | 40% | 40 |
| Nanocomposite + Catalyst | Explosive | 30 | 213% | 25 |
| Nanocomposite + Catalyst | Cyclohexane | 21 | 44% | 30 |

The single laminate sensor is sensitive to explosive stimulant signature. The sensitivity increases with the presence of a catalytic dopant and with a slight increase in device temperature. The sensor is also sensitive to cyclohexane, another species that is commonly found with explosive materials, although to a somewhat different level.

Uses

From process viewpoint, the teachings of this invention can help reduce the cost of sensor, reduce the material needed, and reduce waste, while increasing the production rate of sensors and enhancing the efficiency and effectiveness of the sensors.

This invention can be specifically utilized to develop and produce products that sense, react, trigger, or adapt to changes to environment in general, and in the chemical composition of a fluid in particular. The invention can be generically applied to develop and produce products that sense, react, trigger, or adapt to changes in the environment such as changes in the thermal state, mechanical state, magnetic state, electromagnetic state, ionic state, optical state, photonic state, chromatic state, electronic state, biological state, or nuclear state, or a combination of two or more of these. As a non-limiting example, if the sensing layers are prepared from thermally sensitive material compositions, rapid response thermal sensors can be produced. In another example, if piezoelectric compositions are used in the sensing layer in a multi-laminate stack, vibration and acceleration sensors can be produced. In yet another example, magnetic compositions can yield rapid response magnetic sensors and magnetoresistive sensors. If the interlayer instead is prepared from compositions that interact with photons, novel chromatic, luminescent, photo detectors and photoelectric devices may be produced. With compositions interacting with nuclear radiation, sensors for detecting nuclear radiation may be produced. In another example, with biologically active interlayers, biomedical sensors may be produced. With insulating interlayers, these devices may be thermally isolated or made safe and reliable. The interlayers can be mixed, as discussed before, to provide multifunctional devices and products. The sensing layers may be cut or left intact for specific applications. The sensing layer may be just one layer or a multitude of as many layers as cost-effectively desirable for the application. The electrode may also be one layer or a multitude of as many layers as cost-effective and necessary for the application. These sensors have performance characteristics desired in chemical, metallurgical, environmental, geological, petroleum, glass, ceramic, materials, semiconductor, telecommunications, electronics, electrical, automobile, aerospace and biomedical applications. Such sensors can be combined with metrology techniques and transducers to produce "smart" products and products that adapt and learn from their environments.

What we claim is:

1. An electroded device comprising a laminated structure, wherein at least one layer comprises a quantum-confined nanocomposite constructed from powder.

2. The device of claim 1, wherein the device is a chemical vapor sensing device.

3. The device of claim 2, wherein the chemical vapor comprises hydrogen.

4. The device of claim 2, wherein the chemical vapor comprises an organic compound.

5. The device of claim 2, wherein the chemical vapor comprises an oxide.

6. The device of claim 2, wherein the chemical vapor comprises a chalcogenide.

7. The device of claim 2, wherein the chemical vapor comprises a nitride.

8. The device of claim 2, wherein the chemical vapor comprises a boride.

9. The device of claim 1, wherein the device is a thermal device.

10. The device of claim 1, wherein the device is a piezoelectric device.

11. The device of claim 1, wherein the device is a photoelectric device.

12. The device of claim 1, wherein the device is a biomedical device.

13. The device of claim 1, wherein the nanocomposite comprises zinc.

14. The device of claim 1, wherein the nanomaterial comprises tin.

15. The device of claim 1, wherein the nanomaterial comprises titanium.

16. The device of claim 1, wherein the nanomaterial comprises strontium.

17. The device of claim 1, wherein the nanomaterial comprises barium.

18. The device of claim 1, wherein the nanomaterial comprises a rare earth element.

19. The device of claim 1, wherein the nanomaterial comprises gallium.

20. The device of claim 1, wherein the nanomaterial comprises a material selected from the group consisting of: iron, antimony and zirconium.

21. The device of claim 1, wherein the nanomaterial comprises silicon.

22. The device of claim 1, wherein the nanomaterial comprises a material selected from the group consisting of: indium, tungsten, tantalum and molybdenum.

* * * * *